United States Patent [19]

Heim et al.

[11] 4,262,686
[45] Apr. 21, 1981

[54] APPARATUS FOR THE ELECTRICALLY CONTROLLED PROPORTIONING AND MIXING OF GASES

[75] Inventors: Ulrich Heim, Reinfeld; Scato Albarda, Mölln, both of Fed. Rep. of Germany

[73] Assignee: Drägerwerk Aktiengesellschaft, Fed. Rep. of Germany

[21] Appl. No.: 50,105

[22] Filed: Jun. 19, 1979

[30] Foreign Application Priority Data

Jul. 20, 1978 [DE] Fed. Rep. of Germany ....... 2831856

[51] Int. Cl.³ ............................................. G05D 11/13
[52] U.S. Cl. ....................................... 137/7; 137/88; 137/101.19; 137/607
[58] Field of Search ...................... 137/88, 91, 92, 100, 137/101.19, 607, 624.2, 1, 7; 251/129

[56] References Cited

U.S. PATENT DOCUMENTS

| | | | |
|---|---|---|---|
| 3,249,115 | 5/1966 | Young | 137/92 |
| 3,762,428 | 10/1973 | Beck et al. | 137/101.19 X |
| 4,162,689 | 7/1979 | Zdrodowski | 137/88 |

*Primary Examiner*—William R. Cline
*Attorney, Agent, or Firm*—McGlew and Tuttle

[57] ABSTRACT

An apparatus for the controlled proportioning of gases to be delivered to a consumer comprises a mixed gas line containing the mixed gases to be delivered to the consumer which is connected to a plurality of separate gas supply lines. Each of the supply lines includes a quick-acting, electrically controlled valve which is controlled by control means which is effective to deliver a control pulse to open and close the valve in accordance with a set time slot pattern. For this purpose, the controller advantageously includes means for sensing the pressure in each of the supply lines and the mixed gas line and for regulating the quick-acting valves in accordance with one or more input signals which are fed to a computer section of a controller which has an actuator section which is operated in accordance with the sensed information and the input signals to carry out the supply of the gases in the set time slot pattern. The controller delivers one pulse per time slot pattern, the minimum length of the pulse being determined by the minimum switching time of the control valve and its maximum length being determined by the division of the time slot pattern. For gas amounts smaller than the corresponding minimum pulse times at each position of the time slot pattern, pulses are delivered only at certain points of the pattern.

6 Claims, 2 Drawing Figures

APPARATUS FOR THE ELECTRICALLY CONTROLLED PROPORTIONING AND MIXING OF GASES

BACKGROUND OF THE INVENTION

1. Field of the Invention

This invention relates, in general, to devices for mixing gases and, in particular, to a new and useful apparatus for the electrically controlled proportioning and mixing of gases.

2. Description of the Prior Art

The arrangement for the electrically controlled proportioning of gases is intended for use in industry and also in medicine as a gas proportioner and mixer wherever electric control signals are available. The contemplated use of quick-acting valves in conjunction with electric control permits a large bandwidth with respect to both proportioned amounts and mixing ratios.

In a prior art device for the automatically controlled proportioning of two or more gases in a predetermined mixing ratio, the gases to be mixed are supplied through separate lines. Inserted in each of these lines ahead of a pressure-controlled valve system is a throttle whereby the gas throughput is determined. The mixing ratio can be changed by replacing these throttles.

The valve systems are controlled by the pressure in a common mixing space disposed downstream from the individual valve systems. Pressure control is effected through a pressure-responsive diaphragm which, held in permanent magnets, reverses whenever minimum pressure or maximum pressure is reached.

The proportioned amount and also the mixing ratio can be varied by changing the throttles. This, of course, can be done only during a shutdown. (Published examined German patent application 22 24 588.)

SUMMARY OF THE INVENTION

The invention has, as its object, a gas-mixing device which permits the mixing ratio to be varied rapidly through electric pulses. Depending on the mode of operation, the gas-mixing device is to be controlled on the basis of either the desired gas consumption or the desired mixed-gas pressure.

This object is accomplished in accordance with the characterizing portions of the claims. To this end, a special pulse modulation technique for gas pulses is used. The starting points are electrically pulsable gas control valves operating between the two defined positions OPEN and CLOSED. In the OPEN position, an amount of gas will flow through the valve in unit time which in the most general case is a function of the absolute gas pressure upstream and downstream of the valve which is proportionate to the smallest cross-sectional opening of the valve. When the valve is pulsed with a squared-wave pulse, an amount of gas is delivered which is proportionate to the duration of that control pulse.

For the purpose of gas mixing, a number of such control valves corresponding to the desired number of gas components is arranged in parallel and is electrically pulsed simultaneously or alternately, or both simultaneously and alternately. The necessary control signals are preferably supplied by a computer, for example, a microprocessor. Each of the valves then proportions one of the gas components by means of a pulse modulation technique, the number and duration of the gas pulses delivered in a unit of time determining the gas flow through each valve.

To obtain defined flow rates, it is necessary that in the most general case the gas pressures measured by means of pressure transducers upstream and downstream of each valve be entered in the computer in order that the gas flow rates in the OPEN position, and hence the height or amplitude of the gas pulses, may be computed.

In practice, the simpler case where the ratio of the two pressures is below a critical value (for example, 0.53 in the case of diatomic gases) will frequently be encountered, with the gas flow through the valve then being a linear function of the pressure upstream of the valve alone. It will then suffice to connect the computer to the pressure transducers located upstream of the various valves to be able to adjust the pulse modulations of the individual valves to one another in such a way that a mixture of known concentration and flow rate is delivered. If means for maintaining the pressure exactly constant are disposed ahead of every valve, the pressure transducers upstream of the valves may be dispensed with altogether.

So far as pulse modulation is concerned, it is possible in principle to vary either the width of the individual gas pulses or the number of pulses per unit time. The number of pulses per unit time may, in principle, be varied by variation of a periodic pulse repetition frequency. In accordance with the present invention, however, the number of pulses delivered per unit time is varied, not by variation of a periodic pulse repetition frequency but by omitting individual pulses from a fixed time slot pattern that is common to all valves, this procedure being further combined with a pulse width modulation.

The fixed time slot pattern is given by a maximum contemplated pulse repetition frequency. When fewer pulses are required than the number corresponding to that maximum frequency, one or more pulses are omitted so that gaps occur in the periodic pulse repetition pattern. The pulses of a gas component to be added to the mixture are then preferably triggered so that these pulse-free gaps in the time slot pattern are filled by them.

Starting with a minimum predetermined pulse width, the pulse widths of the individual gas pulses may be increased continuously or in multiples of the basic width until the period of the maximum contemplated repetition frequency is reached. At that pulse width, and with all segments of the time slot pattern occupied by a gas pulse, a valve so pulsed would in practice be permanently open.

Appropriate combinations of pulse-width and pulse-code modulation, in accordance with the examples, permits the representation of a wide dynamic range of variable gas concentrations and gas flow rates. This arrangement offers the advantage, over the straight frequency modulation of a periodic sequence of pulses of fixed width, that the maximum number of pulses per unit time may be kept much smaller with high gas flow rates without the selected time-slot-pattern frequency ever being exceeded. And, over straight pulse-width variation with a fixed repetition frequency, the invention offers the advantage of a greater dynamic mixing range, which otherwise would be severely limited by the minimum realizable pulse width. Finally, the choice of fixed time-slot-pattern division is consistent with the structure of computers with built-in time standard and permits the simple synchronization of the pulses of the various parallel-connected valves so that all of the pulses are distributed substantially uniformly with respect to time and phases of heavy pulse accumulation do not alternate with phases of few pulses, which could result in troublesome fluctuations in supply to the consumer.

The controlling parameters in the design of a pulse-modulation mixer are the minimum bandwidth and the maximum pulse repetition frequency or time slot pattern. A lower limit is imposed on the minimum pulse width by the technical capabilities of the valve, and an upper limit by the requirement that the amount of gas delivered per pulse be small in relation to the characteristic volume of the consumer. When the mixer is used for respiratory purposes, for example, the characteristic volume of the consumer might be the tidal air. The technical capabilities of the valve are limited by its switching times. If the on and off times are identical and pulse thus is symmetric, the width of the square-wave pulse may be regarded as the effective gas-pulse width. In practice, it is desirable that the minimum pulse width correspond to several switching times.

The choice of the time slot pattern, and hence of the maximum pulse repetition frequency, is determined by the following considerations. On the one hand, the maximum frequency should be chosen as low as possible in order to minimize valve wear and to give the computer enough time for computing the next pulse constellation. On the other hand, the repetition frequency must correspond to at least three times the bandwidth which the mixer is expected to have.

In addition to the gas-mixing capabilities provided by the pulse modulations described, provision for varying mixture and amount may further be made through variable gas-pulse heights. Through such expansion of the system, even the most extreme demands made on the dynamic range of the mixer may be met.

Apart from the advantages of its special pulse modulation technique and general pulsability already mentioned, the described arrangement for the mixing of gases offers the advantage that it is assembled from simple components. Conventional globe valves, for example, may be used as quick-acting gas control valves.

The arrangement provides a gas mixing method which permits very rapid concentration changes since mixing tanks which have to be rinsed, are eliminated. With appropriate pulsing by the computer, the arrangement in accordance with the invention may be employed either as a gas-proportioning control element or to dispense, passively, the mixed-gas amounts called for by the consumer. In the latter mode of operation, a pressure transducer in the output line of the mixer would cause the computer to bring up mixed as as soon as the pressure in the line dropped below a preset level.

Accordingly, it is an object of the invention to provide an apparatus for the controlled proportioning of gases to be delivered to a consumer which comprises a mixed gas line containing mixed gases adapted to be delivered to the consumer, a plurality of separate gas supply lines connected into the mixed gas line, a quick-acting electrically controlled valve in each of said separate gas supply lines and controller means connected to each of said quick-acting valves which are effective to deliver a control pulse to open and close said valves in accordance with a set time slot pattern.

A further object of the invention is to provide apparatus for the controlled proportioning of gases which is simple in design, rugged in construction and economical to manufacture.

For an understanding of the principles of the invention, reference is made to the following description of typical embodiments thereof as illustrated in the accompanying drawings.

GENERAL DESCRIPTION OF THE PREFERRED EMBODIMENTS

Figure 1:
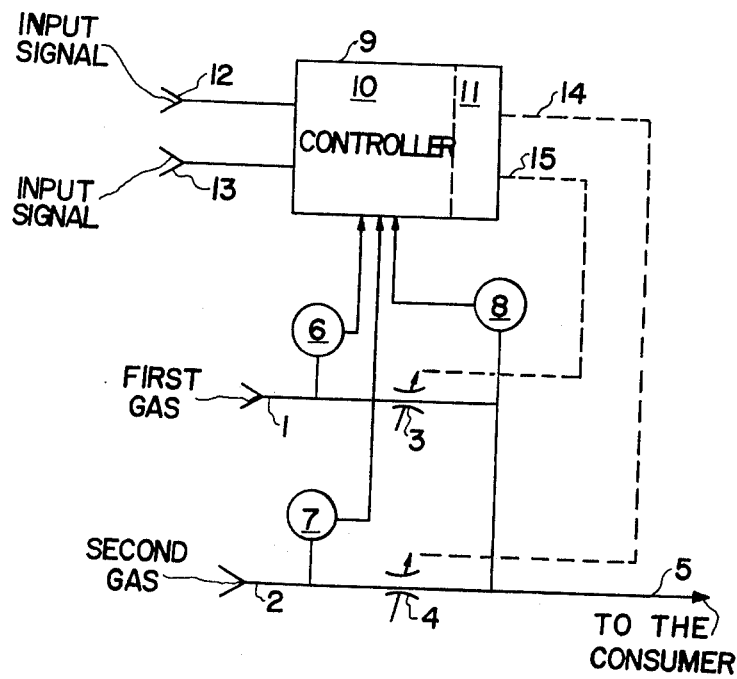
FIG. 1 is a schematic diagram of an apparatus for the controlled proportioning of gases constructed in accordance with the invention.

In accordance with the invention, there is provided an apparatus for the controlled proportioning of gases to be delivered to a consumer and which comprises a mixed gas line 5 as shown in FIG. 1 containing mixed gases adapted to be delivered to the consumer and which is connected to a plurality of separate gas supply lines, in this case, two lines, 1 and 2, which connect into the mixed gas line. Quick-acting electrically controlled valves 3 and 4 are arranged in the supply lines 1 and 2, respectively. Controller means in the form of a controller 9 is connected to operate each of said quick-acting valves 3 and 4 to open and close the valves in accordance with a set time slot pattern.

In FIG. 1, a first gas is supplied through line 1, and a second gas through line 2, at gas supply pressures which are atmospheric pressure. The gas supply pressures are measured by means of pressure transducers 6 and 7 in the respective lines 1 and 2. Through the control valves 3 and 4, constructed as globe valves and disposed in the respective lines 1 and 2, the gases reach the common mixed-gas line 5 which leads to the consumer. The gas pressure in the mixed-gas line 5 is measured by means of the pressure transducer 8 disposed in the line 5. The pressure transducers 6, 7 and 8 deliver electric signals to a controller 9. The controller 9 comprises the computer section 10 and the actuator section 11 for actuation of the control valves 3 and 4 through the actuation lines 14 and 15. Since the valves 3 and 4 are switched only between the OPEN and CLOSED positions and in the OPEN position allow a gas flow $$\dot{v} = c \cdot f(p), \tag{1}$$

the mean flow rate is $$\bar{\dot{v}} = c_1 \cdot \tau_1 \cdot f(p_1) + c_2 \cdot \tau_2 \cdot f(p_2) \tag{2}$$

$\tau_1$ and $\tau_2$ being the ratio of open time to total time. In the computer section 10 of the controller 9, the open ratios $\tau_1$ and $\tau_2$ of the valves 3 and 4 are computed to give a predetermined flow rate $\dot{v}_s$ and a predetermined mixing ratio k.

$$\dot{v}_s = \dot{v}_1 + \dot{v}_2 \tag{3}$$
$$k = \dot{v}_1/(\dot{v}_1 + \dot{v}_2) \tag{4}$$

When the valves 3 and 4 are set in the same way, $$c_1 = c_2 = c. \tag{5}$$

Equation (2) then becomes $$\bar{\dot{v}} = c[\tau_1 \cdot f(p_1) + \tau_2 \cdot f(p_2)] \tag{6}$$

and Equations (4) and (6) become $$\tau_2 = \tau_1 \cdot \frac{f(p_1)}{f(p_2)} \cdot \frac{1-k}{k}. \tag{7}$$

The controller 9 always requires one input signal per valve, which means that in the present case, with the valves 3 and 4, there are two input signals 12 and 13. As input signals 12 and 13, $\dot{v}_s$ and $k_s$ may be chosen. However, in place thereof $\dot{v}_{1,s}$ and $\dot{v}_{2,s}$, or $p_{8,s}$ and $k_s$, or $p_{8,s}$ and $v_{1,s}$ may be selected. Also, one or both values may be permanently stored in the computer section 10.

The electrical signals delivered by the pressure transducers 6, 7 and 8 influence the controller 9. The computer section 10 allows for the fact that the flow is supercritical and therefore is a function of $p_6$ alone so long as (in the case of diatomic gases)

$$p_8/p_6 \leq 0.53,$$

and that the flow is a function of the pressure difference on both sides of the valve in accordance with $$\dot{v}_1 = c\sqrt{\Delta p_1} = c\sqrt{p_6 - p_8}$$

when (in the case of diatomic gases)

$$p_8/p_6 > 0.53.$$

In the case of artificial respiration, the patient very often needs, in addition, an increased oxygen content in the gas for breathing. Air is then supplied through line 1, and oxygen through line 2. The curve 16 in FIG. 2 gives the predetermined total flow $\dot{v}_s$, and the curve 17 the oxygen component $k_{O2,s}$.

The control parameters are based on the following factors: Globe valves for respiratory purposes permit an operating cycle to be executed in one millisecond, with from 1 to 2 ml of gas being dispensed. This amount of gas is so small that its sudden dispensation will not be troublesome to the patient. In respiration, it will suffice to realize a required-flow curve 16 with a control bandwidth of 20 Hz. A pulse repetition frequency of $3 \times 20$ Hz $= 60$ Hz must then be chosen. With minimum pulses of 1.5 ml, this means a flow rate of 5.4 ltr/min. Flow rates greater than 5.4 ltr/min can be obtained by increasing the pulse width. In this range, a bandwidth of 20 Hz thus can actually be realized. Flow rates of less than 5.4 ltr/min can be obtained only be reducing the number of minimum pulses. As a rule, a determination is made in the computing section 10 whether or not a gas pulse is to be delivered in a given 60-Hz period. The bandwidth of 20 Hz cannot then be maintained any longer, which, however, is not a drawback with such small flow rates.

Figure 2:
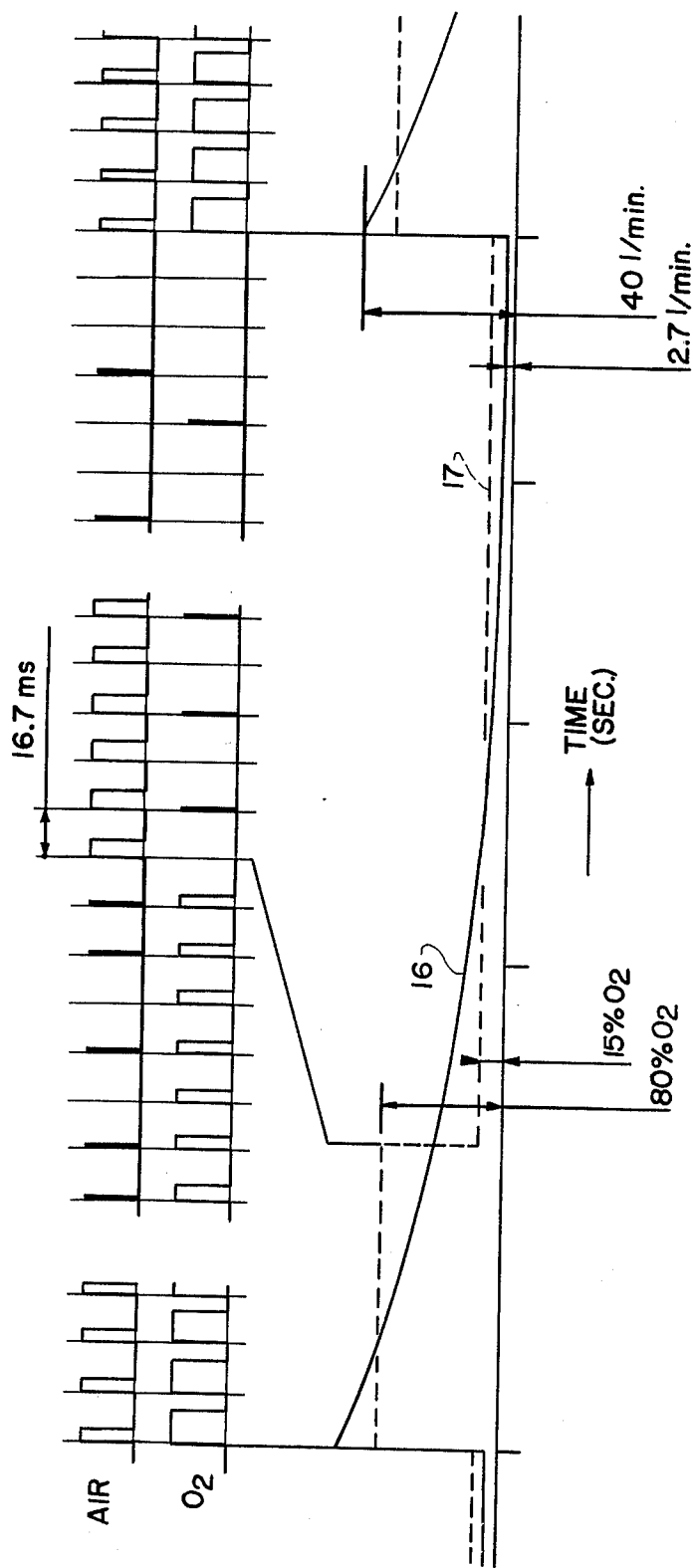
FIG. 2 is a curve showing the control characteristics of the mixing gases for use in a respirator.

The effect this has, in a particular case, on the pulse-width or pulse-frequency modulation of the two valves is apparent from the two upper curves in FIG. 2. It should be noted that in the upper curves the time scale is shown with about 12 X magnification; in other words, only segments are shown.

While specific embodiments of the invention have been shown and described in detail to illustrate the application of the principles of the invention, it will be understood that the invention may be embodied otherwise without departing from such principles.

What is claimed is:

1. An apparatus for the controlled proportioning of gases from separate gas supply sources to be delivered to a consumer, comprising, a mixed gas line containing mixed gases made up of proportioned quantities of separate gases from the separate gas supply sources adapted to be delivered to the consumer, a plurality of separate gas supply lines connected to said mixed gas line, a quick-acting controlled valve in each of said separate gas supply lines operable for switching between an open position for passing gas to said mixed gas line and a closed position in which gas is not passed to said mixed gas line, and controller means connected to each of said quick-acting controlled valves effective to deliver control pulses to said valves for alternately opening and closing said valves in accordance with a set pulse constellation having a selected pulse frequency, said controller means being operable to delete any number of pulses from the pulse frequency for forming the constellation, the minimum width of each pulse being determined by the minimum switching time of respective ones of said valves and the maximum length being determined by the pulse frequency with the pulse width being variable to increase and decrease the flow of gas through each valve respectively, wherein, for gas amounts smaller than those corresponding to the minimum pulse width, pulses are deleted from the constellation.

2. An apparatus according to claim 1, including pressure sensor means in each of gas supply lines and in said mixed gas line connected to said controller means, said controller means being operable responsive to the pressure for regulating the valves.

3. An apparatus according to claim 2, wherein said plurality of separate gas supply lines comprises first and second gas supply lines, said pressure sensor means comprises a pressure sensor in each of said first and second gas supply line and in said mixed gas supply line all connected to said controller means, and said controller means including means for receiving two input signals thereto corresponding to proportioned amounts of gas to be supplied from each of said gas supply lines.

4. An apparatus according to claim 1, wherein said controller means deletes pulses of one of said valves corresponding to a supply of one gas in a pulse constellation for that one gas at times when corresponding pulses are not deleted in a pulse constellation for another gas.

5. A method of proportioning the relative amounts of different gases fed from different supply lines into a common mixed gas line with controllable valves in each of the gas supply lines openable in pulses to supply quantities of gas to the mixed gas line comprising, grouping the pulses for the control of the respective valves into pulse constellations for each respective valve, with the minimum width of each pulse of each constellation being determined by a minimum switching time for a respective one of the valves and the maximum width of each pulse being determined by a fixed pulse frequency, fixing the pulse frequency at a selected value, varying the width of pulses in each pulse constellation for changing gas supplied by each of the valves respectively, and deleting any number of pulses from each of the pulse constellations for reducing a flow of gas from each of the valves respectively further than possible from a reduction of the pulse width alone.

6. A method according to claim 5, wherein pulses are deleted from one constellation at times when corresponding pulses are not deleted in another pulse constellation.

* * * * *